United States Patent [19]

Callahan et al.

[11] 4,069,224

[45] Jan. 17, 1978

[54] NOVEL BENZAMIDES

[75] Inventors: William A. Callahan, Richland Township, Kalamazoo County; Eldridge Myles Glenn, Kalamazoo; Douglas L. Rector, Parchment, all of Mich.

[73] Assignee: The Upjohn Company, Kalamazoo, Mich.

[21] Appl. No.: 590,032

[22] Filed: June 25, 1975

Related U.S. Application Data

[63] Continuation-in-part of Ser. No. 428,364, Dec. 26, 1973, abandoned.

[51] Int. Cl.$^2$ ............................................. C07D 213/81
[52] U.S. Cl. ..................... 260/295 AM; 260/295.5A; 260/294.9; 424/263
[58] Field of Search ................ 260/295 AM, 295.5 A; 424/263

[56] References Cited

U.S. PATENT DOCUMENTS

| | | | |
|---|---|---|---|
| 2,776,294 | 1/1957 | Rey-Bellet et al. | 260/295 AM |
| 2,870,156 | 1/1959 | Perron et al. | 260/295 AM |
| 3,037,988 | 6/1962 | Semb et al. | 260/295 AM |
| 3,367,940 | 2/1968 | Hotten | 260/295 AM |
| 3,439,019 | 4/1969 | Sarett et al. | 260/295 AM |
| 3,455,940 | 7/1969 | Stecker | 260/295 AM |
| 3,509,166 | 4/1970 | Wright, Jr. et al. | 260/295 AM |
| 3,532,704 | 10/1970 | Suter et al. | 424/274 |
| 3,923,820 | 12/1975 | Roldan et al. | 260/295 AM |

FOREIGN PATENT DOCUMENTS 2,329,895  1/1974  Germany.

OTHER PUBLICATIONS

Sam, J. Pharm. Sci. (1967) 56, No. 9, pp. 1202–1205.
Hankovszky et al., J. Med. Chem. (1966) 9, pp. 151–153.
Graf et al., Chemical Abstracts, 30:75764 (1936).
Dorsey et al., J. Pharm. Sci. (1971) 60, No. 11, pp. 1723–1725.

*Primary Examiner*—Norman A. Drezin
*Attorney, Agent, or Firm*—Martin B. Barancik; Roman Saliwanchik

[57] ABSTRACT

A method of improving the endogenous production of prostaglandins by a mammal is disclosed, which comprises administering to the mammal an effective amount of an N-(pyridylalkyl)benzamides. Disclosed also are novel N-(pyridylalkyl)benzamides and therapeutic compositions thereof which are useful in carrying out the method of the invention.

Disclosed also are methods of treating mammals for clinical conditions responsive to prostaglandins, such as for example, male infertility, epidermal injuries, atonic uterine bleeding, thromboembolic disease and like clinical conditions.

29 Claims, No Drawings

NOVEL BENZAMIDES

CROSS REFERENCE TO RELATED APPLICATIONS

This application is a continuation-in-part application of our co-pending application Ser. No. 428,364, filed Dec. 26, 1973, and now abandoned.

BACKGROUND OF THE INVENTION

1. Field of the Invention

The invention is concerned with the production of endogenous prostaglandins by mammals and more specifically concerns a method of raising prostaglandin production levels in the mammal by administering N-(pyridylalkyl)benzamides. The invention also concerns a novel group of N-(pyridylalkyl)benzamides and therapeutic compositions thereof

2. Description of the Prior Art

Natural prostaglandins are a well-known group of physiologically active unsaturated hydroxy-substituted fatty acids which are biosynthesized endogenously by mammals such as, for example, canines, bovines, equines, swine, and humans. Identified roles of the natural prostaglandins in mammalian physiology are illustrated by their action as mediators in the inflammatory process, as tonal agents in effecting the contractility of smooth muscle and as activators in a wide variety of mammalian reproductive processes.

Structurally, the natural prostaglandins have been arbitrarily classified into four basic families termed "PGE", "PGF", "PGA" and "PGB", respectively. The various families are composed of differing analogs and stereoisomers having a hypothetical parent structure, prostanoic acid. For example, the principal members of the PGE family are $11\alpha$, 15-dihydroxy-9-keto-prosta-13-enoic acid (referred to alternatively for convenience as "$PGE_1$"); $11\alpha,15$-dihydroxy-9-keto-prosta-5,13-dienoic acid (hereinafter referred to alternatively as "$PGE_2$"); and $11\alpha,15$-dihydroxy-9-keto-prosta-5,13,17-trienoic acid (referred to alternatively for convenience as "$PGE_3$"). The principal members of the PGF family are $9\alpha,11\alpha,15$-trihydroxy-prosta-13-enoic acid (referred to alternatively for convenience as "$PGF_{1\alpha}$"); $9\beta,11\alpha,15$-trihydroxy-prosta-13-enoic acid (referred to alternatively for convenience as "$PGF_{1\beta}$"); $9\alpha,11\alpha,15$-trihydroxy-prosta-5,13-dienoic acid (hereinafter referred to alternatively for convenience as "$PGF_{2\alpha}$"); $9\beta,11\alpha,15$-trihydroxy-prosta-5,13-dienoic acid (referred to alternatively as "$PGF_{2\beta}$"); and $9\alpha,11\alpha,15$-trihydroxy-prosta-5,13,17trienoic acid (referred to alternatively as "$PGD_{3\alpha}$").

Physiological activity of specific natural prostaglandin compounds may be the same, different in degree or differ from the physiologic activity of other specific natural prostaglandins. It would appear however that they all share a common property in not being continually produced and released by the mammalian tissues of origin. Instead, the prostaglandins appear to be spontaneously synthesized in situ (biosynthesis being equivalent to release) in response to certain stimuli or "trigger" mechanisms. The naturally occurring prostaglandins generally exhibit an extremely short biological half-life and current knowledge indicates that there is no storage of prostaglandins in both tissues or fluids, with the possible exception of seminal fluids. It has been suggested that the trigger or stimulus for endogenous prostaglandin synthesis is associated with trauma of cellular membranes. Such trauma may occur through physical or chemical activity. For example, in the normal mammal carrying a fetus, circulating blood and amniotic fluids do not contain significant amounts of the prostaglandins $PGE_2$ and $PGF_{2\alpha}$ until birth is imminent. At that time the levels of $PGE_2$ and $PGF_{2\alpha}$ which are produced by placental and uterine tissues rise substantially. The suggested function of the prostaglandins at this stage of pregnancy is to stimulte uterine contractions, i.e., labor induction. As another example, injury to mammalia epidermal tissue triggers the in situ synthesis of $PGE_2$ at the site of injury. $PGE_2$ is known to promote and accelerate healing of epidermal wounds (see for example U.S. Pat. No. 3,711,515 at column 5, lines 1–11).

We have discovered that the quantity of prostaglandins produced endogenously by a mammal following the stimulation of biosynthesis will be greatly enhanced, e.g., by from 5 to 10 percent to several times normal production, when certain N-(pyridylalkyl)benzamides have been systemically administered to the mammal prior to the stimulation of biosynthesis by normal trigger mechanisms.

Prior to our invention, there was a suggestion that thrombin caused an increase in the production levels of $PGE_2$ and $PGF_{2\alpha}$ by mammalian blood platelets (Smith et al., Nature New Biol., 231, 235).

Prior to our invention the treatment of clinical conditions responsive to the presence of prostaglandins had been limited to the administration of prostaglandins from exogenous sources. The method of our invention has a number of advantages over the administration of exogeneous prostaglandin. For example as mentioned above the biological half-life of the naturally occurring prostaglandins is extremely short. Illustratively, it has been reported that after about 20 minutes, 500 μg. of $PGF_{2\alpha}$ administered intravenously to an adult human cannot be detected in the body. Therefore to treat clinical conditions such as epidermal injury with exogenous sources of prostaglandins, it is necessary to employ a continuous administration of the desired prostaglandin over a prolonged period of time. By our method, therapeutic levels of prostaglandin are delivered at the "target site" or site of injury with maximum efficiency. Sustained high levels of prostaglandin are observed for several hours following treatment according to our method thus eliminating the need for continuous exogenous prostaglandin administration over long periods of time. In addition the systemic administration of exogenous prostaglandins delivers the therapeutic to organs and tissues other than those at the desired target site. This may result in undesirable responses or "side-effects". By the method of our invention, therapeutic levels of natural prostaglandins are produced at the target site, i.e., at the point of epidermal injury or at the locality stimulating synthesis. This reduces the likelihood of responses in remotely located tissues, minimizing side-effects.

Prior hereto, a number of N-(pyridylalkyl)benzamides were known. For example, Graf, J. Prakt, Chem. 146, 88 (1936) disclosed N-(4-pyridylmethyl)benzamide, the 2- and 3-pyridylmethyl isomers thereof, corresponding nitro- and amino-substituted benzamides and p-nitro-N-[4-methyl-(3-pyridylmethyl)benzamide. Sam, J. Pharm. Sci., 56 (9), 1202 (1967) disclosed the preparation of p-methoxy-N-(p-ethoxyphenyl)-N-(2-pyridylethyl)benzamide and Suter et al., German Offenlegenshrift No. 1,803,569 discloses a number of alkyl- and alkoxy-N-(pyridylmethyl)benzamides. Similarly, Hankovszky et al., J. Med. Chem., 9, 151 (1966) disclosed trimethoxy-N-(2-pyridylethyl)benzamide; see also U.S. Pat. No. 3,037,988 describing a number of alkoxy-N-(pyridylmethyl)benzamides and alkyl, amino and alkylamino-substituted analogs thereof.

SUMMARY OF THE INVENTION

The invention comprises a method of increasing the production of endogenous prostaglandins by a mammal which comprises administering to said mammal an effective amount of a compound selected from those of formula:

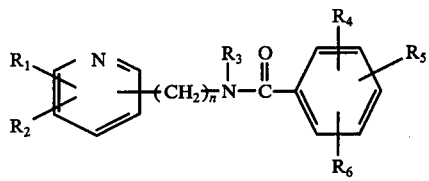

pyridyl N-oxides thereof and pharmaceutically acceptable acid addition salts thereof wherein $R_1$ and $R_2$ are each selected from hydrogen, halogen, hydrocarbyl of 1 to 6 carbon atoms, inclusive, alkoxy, alkylthio, nitro, amino, alkylamino, dialkylamino, acylamino and trihalomethyl; $R_3$ is selected from hydrogen, lower alkyl, cycloalkyl, aryl, aralkyl, and aryl substituted with a group selected from halogen, lower alkoxy, halogen-substituted lower alkyl and halogen-substituted lower alkoxy; $R_4$ is selected from hydrogen, bromine, fluorine, iodine, hydrocarbyl, alkoxy and halogen-substituted hydrocarbyl; $R_5$ is selected from nitro, cyano, amino, acylamino, alkylamino, dialkylamino, phenylazo, alkylthio, arylthio, aryloxy and a group $R_4$ as previously defined; $R_6$ is selected from chlorine, halosulfonyl and a group $R_5$ as defined above; and $n$ is an integer of from 1 to 2, inclusive.

Preferred for carrying out the method of the invention are those compounds (I) having the more specific formula:

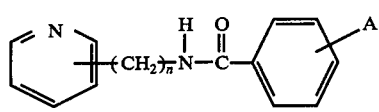

pyridyl N-oxides and pharmaceutically acceptable acid addition salts thereof wherein $n$ is as defined above and A is selected from halogen, lower alkyl and nitro. Most preferred for carrying out the method of the invention are those of the formula:

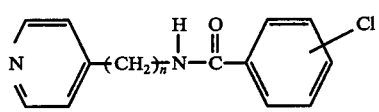

pyridyl N-oxides and pharmaceutically acceptable acid addition salts thereof wherein $n$ is as defined above. Of those of the formula (IIB), 2-chloro-N-(4-pyridylmethyl)-benzamide is the most preferred.

The invention also comprises novel compounds within the scope of formula (I) and having the formula (I) provided that when $R_4$, $R_5$ and $R_6$ are each hydrogen or when $R_4$ and $R_5$ are hydroen and $R_6$ is selected from alkyl, amino and nitro, then at least one of $R_1$ and $R_2$ is selected from halogen, phenyl, alkoxy, alkylthio, alkylamino, dialkylamino, acylamino and trihalomethyl; and the pharmaceutically acceptable acid addition salts thereof.

Preferred novel compounds for use in the method of the invention are those of the more specific formula:

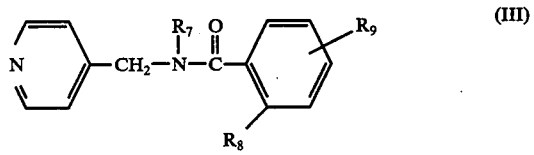

and the pharmaceutically acceptable acid addition salts thereof wherein $R_7$ is selected from hydrogen, lower alkyl cycloalkyl, aryl and aralkyl; and $R_8$ is selected from halogen and mono to tri halogen-substituted hydrocarbyl; $R_9$ is selected from hydrogen, halogen, cycloalkyl, alkenyl, aryl, aralkyl, mono to tri halogen-substituted hydrocarbyl, cyano, acylamino, alkylamino, dialkylamino, phenylazo, alkylthio, arylthio, aryloxy and halosulfonyl.

More preferred novel compounds for use in the method of the invention are those of formula III where $R_7$ is selected from hydrogen and lower alkyl, $R_8$ is selected from halogen and mono to tri halogen-substituted hydrocarbyl of one to six carbon atoms, inclusive. $R_9$ is selected from hydrogen, halogen and mono to tri halogen-substituted hydrocarbyl of one to six carbon atoms, inclusive.

The term "halogen" is used herein in its conventional sense as embracive of chlorine, bromine, fluorine and iodine and the ter "halo" means chloro, bromo, fluoro and iodo, respectively.

The term "hydrocarbyl" is used throughout the specification and claims as meaning the monovalent moiety obtained by removal of a hydrogen atom from a parent hydrocarbon which contains 1 to 12 carbon atoms. Illustrative of such moieties are alkyl of 1 to 12 carbon atoms, inclusive such as methyl, ethyl, propyl, butyl, pentyl, hexyl, heptyl, octyl, nonyl, decyl, undecyl, dodecyl and isomeric forms thereof; cycloalkyl of 3 to 8 carbon atoms, inclusive, such as cyclopropyl, cyclobutyl, cyclopentyl, cyclohexyl, cycloheptyl, cyclooctyl and the like; alkenyl of 2 to 12 carbon atoms, inclusive; such as vinyl, allyl, butenyl, pentenyl, hexenyl, heptenyl, octenyl, nonenyl, decenyl, undecenyl, dodecenyl and isomeric forms thereof; aryl of 6 to 12 carbon atoms, inclusive, such as phenyl, tolyl, xylyl, naphthyl, biphenylyl and the like, aralkyl of 7 to 12 carbon atoms, inclusive, such as benzyl, phenethyl, phenpropyl, phenbutyl, phenpentyl, phenhexyl and the like.

The terms "alkyl", "aryl", "cycloalkyl" and "aralkyl" as used in this specification and claims are those terms as defined above.

The term "halogen-substituted hydrocarbyl" means hydrocarbyl as defined above wherein one or more hydrogen atoms have been replaced with a halogen atom as defined above. Illustrative of halogen-substituted hydrocarbyl are trichloromethyl, bromocyclobutyl, 1,2-diiodovinyl, chlorophenyl, p-chlorobenzyl and the like.

The term "alkoxy" is used herein to mean the monovalent moiety of the formula

—O—alkyl wherein alkyl is as described above. Illustrative of alkoxy are methoxy, ethoxy, butoxy, pentyloxy, heptyloxy, decyloxy, dodecyloxy, and the like.

The term "aryloxy" is used herein to mean the monovalent moiety of formula:

aryl—O— wherein aryl is as defined above. Illustrative of aryloxy are phenoxy, naphthoxy and the like.

The term "alkylthio" means the monovalent moiety of formula:

alkyl—S— wherein alkyl is as defined above. Representative of alkylthio are methylthio, pentylthio, dodecylthio and the like.

The term "arylthio" as used herein means the monovalent moiety of formula:

aryl—S— wherein aryl is as defined above. Illustrative of arylthio are phenylthio, naphthylthio and the like.

The term "alkylamino" is used herein to mean an amino group wherein one hydrogen has been replaced with an alkyl group as previously defined. Illustrative of alkylamino are methylamino, butylamino, dodecylamino and the like.

The term "dialkylamino" is used to mean an amino group wherein both hydrogen atoms have been replaced with alkyl groups as defined above. Illustrative of dialkylamino are groups such as dimethylamino, ethylhexylamino, didodecylamino and the like.

The term "acylamino" as used herein means the monovalent moiety of formula:

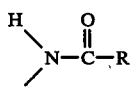

wherein R is alkyl as previously defined.

The term "lower alkyl" means alkyl as previously described having 1 to 4 carbon atoms, inclusive, and the term "lower alkoxy" means alkoxy as defined above having 1 to 4 carbon atoms, inclusive.

The term "halogen-substituted lower alkyl" means lower alkyl as defined above wherein one or more of the hydrogen atoms have been replaced with halogen as previously defined. Illustrative of such groups are chloromethyl, trifluoromethyl, 1,2-dibromomethyl, 1,1,3,3-tetrachloropropyl and the like.

The term "halogen-substituted lower alkoxy" means lower alkoxy as defined above, wherein one or more hydrogen atoms have been replaced with a halogen atom. Illustrative of such halogen-substituted groups are 1-chloroethoxy, 1,2-dibromobutoxy and the like.

The term "halosulfonyl" as used herein means the monovalent moiety of formula:

Halogen—SO$_2$— wherein halogen is as defined above.

One skilled in the art will appreciate a variety of useful procedures which may be carried out by using the method of our invention. For example, natural prostaglandins are sought after for biological studies and as therapeutics in the treatment of mammals for a variety of clinical conditions. The extraction and recovery of natural prostaglandins from animal tissuues such as lung tissue, male accessory genital glands and the like from sacrificed animals is a costly procedure and any improvement of yields is a significantly valuable commercial factor. By the method of our invention, effective amounts of compounds of the formula (I) are administered to the natural prostaglandin producing animal within a period of from 1 to about 6 hours prior to sacrifice. This results in enhanced yields of prostaglandins recovered by the conventional and known methods of extraction.

By the method of our invention, mammal treatment procedures for a variety of clinical conditions responsive to prostaglandins are improved. More specifically, those clinical conditions which are related to a prostaglandin deficiency or which respond to enhanced levels of prostaglandins and in which there is an operative trigger mechanism for stimulation of prostaglandin production are advantageously responsive to the method of our invention. Illustratively, some 13 different prostaglandins, representing all four prostaglandin families are found in mammalian seminal fluids. A correlation exists between low prostaglandin levels (particularly of the PGE family) in seminal fluids and male infertility; see for example "The Prostaglandins", Karim, Medical and Technical Pub. Co. Ltd., Oxford (1972) pp. 134-6. In those instances wherein seminal fluid prostaglandins are being produced by the mammal but in low quantity, production levels are raised by the method of our invention. Thus, the method of our invention provides a method of treating mammalian male infertility which comprises administering to said male an effective amount of a compound (I) or a pyridyl N-oxide or a pharmaceutically acceptable acid addition salt thereof.

To further illustrate the use of the method of our invention, it is known that the prostaglandin PGE$_2$ is produced at the site of epidermal injury in a mammal [see for example Anggard et al., Alza Conference on Prostaglandins in Cellular Biology, Edited by Ramwell and Phariss, Plenum Press, N.Y., N.Y. (1972), page 269]. The generally accepted role of PGE$_2$ at the site of injury following for example burns, abrasions, surgery, penetration wounds and like epidermal injuries is to stimulate epidermal cell proliferation and keratin formation, thereby accelerating wound healing. It should be further noted that the term epidermal injury is broad enough in this context to include skin conditions such as psoriasis wherein the PGE$_2$ stimulates production of cyclic AMP which additionally aids in overcoming the effects of the conditions. By using the method of our invention, higher levels of PGE$_2$ are obtained over long periods of time to accelerate the healing process. Thus, a preferred embodiment of the method of our invention comprises a method of promoting the healing of epidermal injuries in a mammal which comprises administering to said mammal an effective amount of a compound selected from those of the formula (I), pyridyl N-oxides thereof and pharmaceutically acceptable acid addition salts thereof. Surprisingly, although PGE$_2$ is a known mediary in the inflammatory process, the method of our invention so employed does not produce a significant increase in the manifestations generally associated with inflammation, such as pain, edema, swelling and like inflammatory manifestations.

In another use, the method of our invention is employed advantageously to prevent or control atonic uterine bleeding. PGE$_2$ and PGF$_{2\alpha}$ are produced by the endometrium and blood platelets (upon aggregation). In situations of post-partum hemorrhage due to an atonal uterus, the elevation of PGE$_2$ and PGF$_{2\alpha}$ production by platelets at the site of bleeding provides therapeutic levels of the two prostaglandins sufficient to render tone to the uterine muscle, thus causing sustained contraction of the uterus and controlling hemorrhage. The method of our invention therefore includes as an embodiment the prevention and control of atonic uterine hemorrhage in a mammal which comprises administering to the mammal an effective amount of a compound selected from those of formula (I), pyridyl N-oxides thereof and pharmaceutically acceptable acid addition salts thereof. Administration of the compound (I), its N-oxides or its salts in this particular use is advantageously carried out during a period of from about 1 to 6 hours before an anticipated hermorrhage to prevent the same, or immediately following the start of hemorrhage. In the latter instance, control generally occuurs within from 1 to about 3 hours of administration.

As mentioned above, $PGF_{2\alpha}$ and $PGE_2$ are produced by the mammalian blood platelet upon stimulation of synthesis by cell aggregation. Build-up of $PGF_{2\alpha}$ and $PGF_2$ levels at the site of platelet aggregation are associated with inhibition of further platelet aggregation, thereby terminating the continued development of thrombi. By the method of our invention one may terminate the development of thrombi earlier and more rapidly through enhanced levels of $PGF_{2\alpha}$ and $PGE_2$ production. This is particularly useful in the treatment and prevention of myocardial infarcts, postoperative thrombosis, atherosclerosis, arteriosclerosis and like clinical conditions where the development of a thrombus is undesired. Thus, another embodiment of our invention comprises a method of controlling the development of a thrombus in a mammal which comprises administering an effective amount of a compound selected from those of formula (I), pyridyl N-oxides thereof and pharmaceutically acceptable acid addition salts thereof, to said mammal.

DETAILED DESCRIPTION OF THE INVENTION

The compounds (I), pyridyl N-oxides thereof and pharmaceutically acceptable acid addition salts thereof are admisistered to the mammal systemically and topically. Illustrative of systemic methods of administration are oral and parenteral. However, a systemic effect can be achieved through a topical administration, such as a rectal suppository. Topical administration in the form of lotions, cream, etc. can also be used for treating conditions such as epidermal injury.

The effective amount administered is that quantity which brings about an increase in the production levels of prostaglandins biosynthesized by the subject mammal. The exact effective amount administered will depend upon a number of factors such as, for example, the specific compound (I), its N-oxide or salt, species of mammal, age, weight and physical condition of the mammal, route of administration and in the instances wherein a specific clinical condition is being treated by the method of the invention, the nature of the conditions. In general prostaglandin production levels rise in direct proportion to the quantity of the compound (I) administered.

The exact dosage requirement for increasing prostaglandin production in a given situation may be determined by administration of a trial dose and observation of the prostaglandin production response by blood plasma analysis or by clinical response to the presence of prostaglandins. In general, an effective amount to be administered is within the range of from about 0.1 mg. to about 500 mg. per kilogram of body weight of the recipient mammal and preferably within the range of from about 5 mg. to about 50 mg. per kilogram body weight. In general, the degree of response is related to dose, and higher doses produce faster and more complete clinical responses. In most instances, a single administration will effect the desired response and bring about the result desired. In cases such as the treatment of epidermal injuries however, it may be desirable to repeat the administrations several times. In instances of repeated administrations we have noted a decrease in degree of prostaglandin production response upon administrations subsequent to the first unless there is a resting period between administrations. Resting periods of from about 12 to about 24 hours between administrations assure the highest prostaglandin production for a given dosage of the compounds (I), their N-oxides and pharmaceutically acceptable acid addition salts.

Although all mammalian tissues capable of producing prostaglandins are responsive to the method of our invention, the most advantageous response is obtained from circulating blood platelets which produce $PGE_2$ and $PGE_{2\alpha}$. The platelets produce larger quantities of these prostaglandins and serve to meet therapeutic needs as described above most readily and conveniently. The method of our invention is particularly advantageous in stimulating high yields of $PGF_{2\alpha}$ from the producing blood platelets.

Illustrative of the known compounds of formula (I) employed in the method of our invention are N-(2-pyridyl-methyl)benzamide, N-(3-pyridylmethyl)benzamide, N-(4-pyridylmethyl)benzamide, N-(6-methyl-3-pyridylmethyl)benzamide, p-nitro-N-(2-pyridylmethyl)benzamide, m-nitro-N-(2-pyridylmethyl)benzamide, p-nitro-N-(6-methyl-3-pyridylmethyl)benzamide, p-amino-N-(2-pyridylmethyl)benzamide, p-amino-N-(4-pyridylmethyl)benzamide, o-amino-N-(3-pyridylmethyl)benzamide, m-amino-N-(3-pyridylmethyl)benzamide, 4-butoxy-2,6-dimethyl-N-(3-pyridylmethyl)benzamide, 3,4,5-trimethoxy-N-(2-pyridylethyl)benzamide p-methoxy-N-(p-ethoxyphenyl)-N-(2-pyridylethyl)benzamide, 3,4,5-trimethoxy-N-(2-amino-6-methyl-3-pyridylmethyl)benzamide, 3,4,5-trimethoxy-N-(5-amino-4,6-dimethyl-3-pyridylmethyl)bennzamide, 3,4,5-trimethoxy-N-(2-n-butylamino-6-methyl-3-pyridylmethyl)-benzamide, 3,4,5-trimethoxy-N-(6-methyl-4-pyridylmethyl)benzamide, 3,4,5-trimethoxy-N-(2-methylamino-6-methyl-3-pyridylmethyl)benzamide, 3,4,5-trimethoxy-N-(6-methyl-3-pyridylmethyl)benzamide, 3,4,5-trimethoxy-N-(2-amino-3-pyridylmethyl)benzamide, 3,4,5-triethoxy-N-(2-amino-6-methyl-3-pyridylmethyl)benzamide and the like.

The compounds of formula (I) are readily prepared by a variety of known methods. A convenient method is that described in U.S. Pat. No. 3,037,988. In general, the method of this patent comprises acylating an appropriate aminoalkylpyridine (IV) with an appropriate benzoyl halide (V). The reaction is conveniently illustrated by the schematic equation:

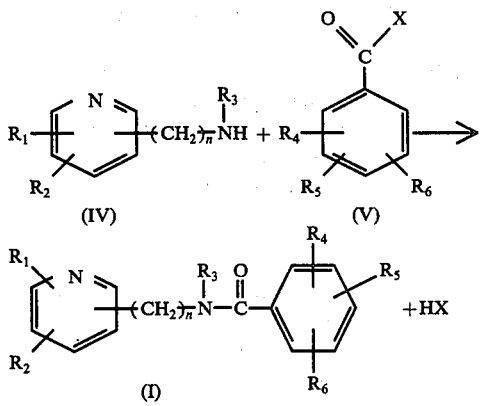

wherein $R_1$, $R_2$, $R_3$, $R_4$, $R_5$, $R_6$ and n are as previously defined; X represents halogen.

In general, the reaction proceeds satisfactorily in the presence of an acid acceptor compound as illustrated by the trialkylamines such as trimethylamine, triethylamine, tripropylamine, tributylamine. Pyridine, potassium carbonate and sodium hydroxide may also be employed as acid acceptors. The illustrated reaction is advantageously carried out within a temperature range of from about −10° C. to about 90° C. and in the presence of an inert organic solvent such as dioxane, pyridine, benzene, acetonitrile, dimethylformamide, dimethylsulfoxide, water, tetrahydrofuran and the like.

Upon completion of the above described reaction, the desired compounds (I) are readily separated from the reaction mixture by conventional methods, i.e., by stripping solvent, filtration, crystallization and like techniques. Complete details of the above described method may be found by referring to U.S. Pat. No. 3,037,988.

The starting aminoalkylpyridines (IV) are generally well known as are methods of their preparation; see for example Sculley et al., J. Am. Chem. Soc., 75, 3400, (1953); Shuman et al., J. Org. Chem., 27, 1970 (1962); Bobbitt et al., J. Org. Chem., 29, 2298 (1964); Bower et al., J. Chem. Soc., 2834(1955); Bruce et al., J. Am. Chem. Soc., 66, 2092 (1944); and Sam, J. Pharm. Sci., 56, 1202 (1967).

A convenient method of preparing the aminoalkylpyridines (IV) wherein $R_1$ and $R_2$ are other than acylamino groups is by reduction of the corresponding amide compounds of formula:

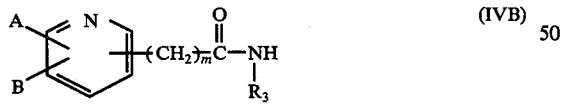

wherein m is an integer of from 0 to 1 and $R_3$ is as defined above; A and B are each selected from hydrogen, halogen, hydrocarbyl of 1 to 6 carbon atoms, inclusive, alkoxy, alkylthio, nitro, amino, alkylamino, dialkylamino and trihalomethyl. The method of reduction is well known, see for example Tarbell et al., J. Am. Chem. Soc., 82, 2657 (1950); Uffer et al., Helv. Chim. Acta., 31, 1397 (1948); and Brown Org. Reactions, Vol. 6, J. Wiley and Sons, N.Y., N.Y. (1951), pg. 469.

Representative of the compounds (IVB) are N-ethyl 2,6-dimethylisonicotinamide, 2-chloro-6-ethylthioisonicotinamide, N-benzyl-4-pyridylacetamide, 2-pyridineacetamide, 4′-phenoxynicotinanilide, 2′-phenylnicotinanilide, 5′-methyl-4′-nitro-o-picolinanisidide, N-butyl-2-ethylthioisonicotinamide, N-butyl-6-chloroisonicotinamide, N-(p-chlorophenyl)isonicotinamide, 2-chloro-6-methoxy-N-(α-methylphenylethyl)isonicotinamide, N-benzylisonicotinamide, 4-cyclohexylnicotinanilide, N-1-naphthylisonicotinamide, 4′-chloroisonicotinanilide, p-isonicotinanisidine, N-[3-(o-chlorophenyl)propyl]isonicotinamide, N-cyclohexylisonicotinamide, 2-chloro-N-(cyclopropylmethyl)isonicotinamide, N-phenylisonicotinamide, N-(diphenylmethyl)isonicotinamide, N-(p-methoxyphenyl)isonicotinamide, 2′-chloro-4′-nitrocopicolinanilide and 2′,5′-diethoxy-4′-nitropicotinanilide, N-(p-trifluoromethylphenyl)isonicotinamide, N-(p-trichloromethoxyphenyl)isonicotinamide, N-butyl-6-methylthiopicolinamide, N-cyclohexylpicolinamide, 4-chloropicolinamide, 4-ethoxypicolinamide, 5-ethylthiopicolinanilide, and the like.

An alternative method of preparing the aminoalkylpyridines (IV) wherein $R_3$ is specifically hydrogen and a method for preparing compounds (IV) wherein $R_1$ and/or $R_2$ are acylamino groups is that disclosed by Sculley et al., supra., which comprises reducing the corresponding nitrile compounds of formula:

wherein $R_1$, $R_2$ and m are as before defined.

Representative of the compounds (IVC) are picolinonitrile, 3-chloropicolinonitrile, 4-methylpicolinonitrile, 4,6-dimethylpicolinonitrile, 4-phenylpicolinonitrile, 4-benzylpicolinonitrile, 3-allylpicolinonitrile, 4-methoxypicolinonitrile, 2,5-diethoxypicolinonitrile, 4-methylthiopicolinonitrile, 3-nitropicolinonitrile, 3,5-diaminopicolinonitrile, 3-ethylaminopicolinonitrile, 3-diethylaminopicolinonitrile, 4-acetylaminopicolinonitrile, 4-trifluoromethylpicolinonitrile, 3-pyridylacetonitrile and the like.

The compounds (IV) wherein $R_1$ and/or $R_2$ are acylamino groups may also be prepared by N-acylation of the corresponding compounds (IV) wherein $R_1$ and/or $R_2$ are amino groups. The methods of such N-acylations are well known, such as by reaction of the appropriate compounds (IV) with an appropriate acyl halide of formula:

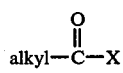

wherein alkyl and X have the meanings previously ascribed to them.

The benzoyl halide reactants (V) are generally well known as illustrated by benzoyl chloride, 3-chlorobenzoyl chloride, 2,5-dichlorobenzoyl chloride, 2-methylbenzoyl chloride, 2,5-diethylbenzoyl chloride, 4-phenylbenzoyl chloride, 2,5-dimethoxybenzoyl chloride, 3-nitrobenzoyl chloride, 3,5-dinitrobenzoyl chloride, 3-aminobenzoyl chloride, 3-methylaminobenzoyl chloride, 3,5-di-(diethylamino)benzoyl chloride, 4-acetylaminobenzoyl chloride, 4-methylthiobenzoyl chloride, 5-trifluoromethylbenzoyl chloride, 4-fluorosulfonylbenzoyl chloride and the like.

The pyridyl N-oxides of the compounds (I), i.e., compounds of the formula:

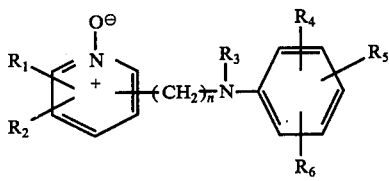

(VI)

wherein $R_1$, $R_2$, $R_3$, $R_4$, $R_5$, $R_6$ and n are as defined above and their pharmaceutically acceptable salts thereof are also a novel class of compounds. They are useful for the same purposes and in the same manner as the corresponding non-oxides. They are readily prepared by oxidation of the corresponding compounds (I) or the pharmaceuticlly acceptable acid addition salts thereof by conventional and known methods such as by oxidation with hydrogen peroxide in the presence of acetic acids; see for example the method described by E. Ochia, Aromatic Amine Oxides, Elsevier Pub. Co., N.Y., N.Y. pg. 25 (1967).

The pharmaceutically acceptable acid addition salts of the compounds (I) and (VI) may be used for the same purposes as the corresponding free base compounds, and in the same manner. They are readily prepared by reacting the free base with a stoichiometric proportion of an appropriate acid. The method is well known to those skilled in the art and may be carried out in aqueous or non-aqueous media such as ethanol, ether, ethyl acetate and the like. Illustrative of pharmaceutically acceptable acid addition salts are those formed upon reaction of the free base compound (I) or compound (VI) with hydrochloric acid, hydrobromic acid, sulfuric acid, phosphoric acid, acetic acid, lactic acid, citric acid, succinic acid, benzoic acid, salicyclic acid, pamoic acid, cyclohexanesulfamic acid and the like.

This invention relates also to pharmaceutical dosage unit forms for systemic and topical administration which are useful in improving the production of endogenous prostaglandins by mammals, including humans. Preferred as the mode of administration are oral and parenteral methods. The term "dosage unit form" as used in this specification and in the claims refers to physically discrete units suitable as unitary dosages for mammalian subjects, each unit containing a predetermined quantity of the essential active ingredient, i.e., a compound of formula (VI); or a compound of the formula (I) provided that when $R_5$, $R_6$ and $R_7$ are each hydrogen, then at least one of $R_1$ and $R_2$ is selected from halogen, phenyl, alkoxy, akylthio, alkylamino, dialkylamino, acylamino and trihalomethyl and further provided that when one of $R_5$, $R_6$ and $R_7$ is selected from alkyl, alkoxy, amino and nitro, then at least one of $R_1$ and $R_2$ is selected from halogen, phenyl, alkoxy, alkylthio, alkylamino, dialkylamino, acylamino and trihalomethyl; or pharmaceutically acceptable acid addition salts thereof; calculated to produce the desired effect in combustion with the required pharmaceutical means which adapt said ingredient for systemic administration. Examples of dosage unit forms in accordance with this invention are tablets, capsules, orally administered liquid preparations in liquid vehicles, sterile preparations in liquid vehicles, sterile preparations in liquid vehicles for intramuscular and intravenous administration, suppositories for topical application, sterile dry preparations for the extemporaneous preparation of sterile injectable preparations in a liquid vehicle, and lotions, creams aerosols, ointments, paste, jellies, sprays, and the like. Solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules, both hard and soft, are formulated with conventional diluents and excipients, for example, edible oils, talc, calcium carbonate, calcium stearate and the like. Liquid preparations for oral administration are prepared in water or aqueous solutions which advantageously contain suspending agents, such as for example, carboxymethylcellulose, methylcellulose, acacia, polyvinyl pyrrolidone, polyvinyl alcohol and the like. In the instance of injectable forms, they must be sterile and must be fluid to the extent that easy syringeability exists. Such preparations must be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example, sugars or sodium chloride. Carriers and vehicles include vegetable oils, ethanol and polyols, for example glycerol, propylene glycol, liquid polyethylene glycol and the like. Any solid preparations for subsequent extemporaneous preparation of sterile injectable preparations are sterilized, preferably by exposure to a sterilizing gas such as for example, ethylene oxide. The aforesaid carriers vehicles, diluents, excipients, preservatives, isotonic agents and the like constitute the pharmaceutical means which adapt the preparations for systemic administration.

For topical use, the compounds can be formulated in a pharmaceutical carrier suitable for application to affected areas of the skin. Accordingly, the compositions of this invention include those pharmaceutical forms in which the medication is applied externally for contact with the area to be treated. Conventional pharmaceutical forms for this purpose include ointments, creams, lotions, solutions, suspensions, pastes, jellies, sprays and aerosols, suppositories, powders and the like. In preparing the desired topical formulations of the novel compound of this invention, various additives, solvents, diluents and adjuvants can be utilized. These illustratively include water, surfactants (e.g., polysorbate 80 polyoxyethylene sorbitan monostearate), emulsifiers (e.g., glyceryl monostearatediethylaminoethyl alkyl amide phosphate, isopropyl myristate and cetyl alcohol), alcohols (e.g., ethanol and isopropanol), lower alkyl diols (e.g., 1,3-butanediol, 2,3-butanediol, 1,2-propanediol, 1,3-propanediol), glycols (e.g., propylene glycol, glycerol, sorbitol), ointment-type bases (e.g., spermaceti, Carbowaxes, beeswax, petrolatum, lanolin), higher fatty acids and alcohols (e.g., stearic acid, stearyl alcohol, cetyl alcohol, palmitic acid), liquid paraffin and vegetable oils (e.g., peanut oil, caston oil), preservatives such as sorbic acid, parabens, chlorocresol, benzalkonium chloride) and solid diluents (e.g., lactose, starch, bentonite, talc).

The pharmaceutical dosage unit forms are prepared in accordance with the preceding general description to provide from about 10 to about 1500 mg. of the essential active ingredient per dosage unit form preferred and from about 100 to about 1000 mg. For topical administration, the essential active ingredient is from about 1 to about 15 weight percent.

The following examples describe the manner and process of making and using the invention, and set forth the best mode contemplated by the inventors of carrying out the invention but are not to be construed as limiting.

EXAMPLE 1

To a mixture of 4.32 gms. (0.04 mole) of 3-aminomethylpyridine, 4.04 gm. (0.04 mole) of triethylamine and 100 ml. of tetrahydrofuran chilled in an ice bath, there is added 7.00 gms. (0.04 mole) of 3-chlorobenzoyl chloride with stirring. After addition, the mixture is stirred at room temperature for 6 hours and then stands 12 hours. The resulting mixture is diluted to 1 liter with water and evaporated to strip solvent. Trituration of the residue oil with water caused solidification of the residue. The solid is crystallized from aqueous ethanol to give 8.54 gms. (87% of theory) of 3-chloro-N-(3-pyridylmethyl)-benzamide in the form of colorless crystals; m.p. 96.7° C.

Similarly, following the above procedure but replacing the 3-chlorobenzoyl chloride as used therein with an equal molar proportion of 4-chlorohexylbenzoyl chloride, 4-phenylbenzoyl chloride, 4-(p-chlorophenyl)benzoyl chloride, 3-cyanobenzoyl chloride, 4-acetylaminobenzoyl chloride, 4-methylaminobenzoyl chloride, 4-diethylaminobenzoyl chloride, 4-methylthiobenzoyl chloride, 4-phenylthiobenzoyl chloride and 4-phenoxybenzoyl chloride, respectively, there is obtained 4-cyclohexyl-N-(3-pyridylmethyl)benzamide, 4-phenyl-N-(3-pyridylmethyl)benzamide, 4-(p-chlorophenyl)-N-(3-pyridylmethyl)benzamide, 3-cyano-N-(3-pyridylmethyl)benzamide, 4-acetylamino-N-(3-pyridylmethyl)benzamide, 4-methylamino-N-(3-pyridylmethyl)benzamide, 4-diethylamino-N-(3-pyridylmethyl)benzamide, 4-methylthio-N-(3-pyridylmethyl)benzamide, 4-phenylthio-N-(3-pyridylmethyl)benzamide and 4-phenoxy-N-(3-pyridylmethyl)benzamide, respectively.

EXAMPLE 2

Following the procedure of Example 1, supra., but replacing the 3-chlorobenzoyl chloride as used therein with an equal molar proportion of 4-chlorobenzoyl chloride there is obtained 8.15 gms. (83 percent of theory) of 4-chloro-N-(3-pyridylmethyl)benzamide in the form of colorless cyrstals, m.p. 126.1° C.

Similarly, following the above procedure but replacing the 3-aminomethylpyridine as used therein with an equal molar proportion of 2-aminomethyl-6-methylpyridine, 2-(2-aminoethyl)-5-ethylpyridine, 3-amino-5-(aminomethyl)-2-methylpyridine, 2-(aminomethyl)-3-chloropyridine, 2-(aminomethyl)-4-phenylpyridine, 2-(aminomethyl)-4-benzylpyridine, 2-(aminomethyl)-4-methoxypyridine, 2-(aminomethyl)-4-methylthiopyridine, 2-(aminomethyl)-3-nitropyridine, 2-(aminomethyl)-3-ethylaminopyridine, 2-(aminomethyl)-3-diethylaminopyridine, 2-(aminomethyl)-4-acetylaminopyridine and 2-(aminomethyl)-4-trifluoromethylpyridine, respectively, all of which may be prepared by reduction of the corresponding nitrile of formula (IVC), supra., there is obtained 4-chloro-N-[2-(6-methylpyridylmethyl)]benzamide, 4-chloro-N-[2-(5-ethylpyridylethyl)]benzamide, 4-chloro-N-[5-(3-amino-2-methylpyridylmethyl)]benzamide, 4-chloro-N-[2-(3-chloropyridylmethyl)]benzamide, 4-chloro-N-[2-(4-phenylpyridylmethyl)]benzamide, 4-chloro-N-[2-(4-benzylpyridylmethyl)]benzamide, 4-chloro-N-[2-(4-methoxypyridyl)]benzamide, 4-chloro-N-[2-(4-methylthiopyridylmethyl)]benzamide, 4-chloro-N-[2-(3-nitropyridylmethyl)]benzamide, 4-chloro-N-[2-(3-ethylaminopyridylmethyl)]benzamide, 4-chloro-N-[2-(3-diethylaminopyridyl)]benzamide, 4-chloro-N-[2-(4-acetylaminopyridylmethyl)]benzamide and 4-chloro-N-[2(4-trifluoromethylpyridylmethyl)]benzamide, respectively.

EXAMPLE 3

Following the procedure of Example 1, supra., but replacing the 3-chlorobenzoyl chloride as used therein with an equal molar proportion of 2-chlorobenzoyl chloride there is obtained 7.39 gms. (75 percent of theory) of 2-chloro-N-(3-pyridylmethyl)benzamide in the form of colorless crystals, m.p. 74.8° C.

EXAMPLE 4

Following the procedure of Example 1, supra., but replacing the 3-chlorobenzoyl chloride as used therein with an equal molar proportion of p-trifluoromethylbenzoyl chloride there is obtained 9.79 gms. (87 percent of theory) of N-(3-pyridylmethyl)-4-trifluoromethylbenzamide in the form of colorless plates, m.p. 130.8° C.

EXAMPLE 5

Following the procedure of Example 1, supra., but replacing the 3-chlorobenzoyl chloride as used therein with an equal molar proporation of 3-fluorobenzoyl chloride there is obtained 6.41 gms. (70 percent of theory) of 3-fluoro-N-(3-pyridylmethyl)benzamide in the form of colorless crystals, m.p. 102.3° C.

EXAMPLE 6

Part A

To a mixture of 5.4 gms. (0.05 mole) of 2-aminomethylpyridine, 5.05 gms. (0.05 mole) of triethylamine and 100 ml. of tetrahydrofuran there is added dropwise with stirring 8.75 gms. (0.05 mole) of 3-chlorobenzoyl chloride. The resulting mixture is stirred for 1 hour and then diulted with water to a volume of 1 liter. The diluted mixture is evaporated to give an oil residue which is 3-chloro-N-(2-pyridylmethyl)benzamide.

Part B

The oil residue of Part A, above, is dissolved in chloroform and the solution washed with water. The organic phase is separated and saturated with hydrogen chloride. Solvent is then stripped leaving a solid residue which upon crystallization from ethanol gives 10.51 gms. (85 percent of theory) of 3-chloro-N-(2-pyridylmethyl)benzamide hydrochloride in the form of colorless needles, m.p. 189.6° C.

EXAMPLE 7

Following the procedure of Example 1, supra., but replacing the 3-aminomethylpyridine as used therein with an equal molar proportion of 2-aminomethylpyridine and replacing the 3-chlorobenzoyl chloride as used therein with an equal molar proportion of 4-chlorobenzoyl chloride there is obtained 6.66 gms. (68 percent of theory) of 4-chloro-N-(2-pyridylmethyl)benzamide in the form of white needles, m.p. 105.3° C.

EXAMPLE 8

To a solution of 4.32 gm. (0.04 mole) of 2-aminomethylpyridine, 5.5 gms. (0.05 mole) of triethylamine and 100 ml. of tetrahydrofuran there is added dropwise with stirring 7.0 gms. (0.04 mole) of 2-chlorobenzoyl chloride. After addition stirring is continued 1 hour and then the mixture is refluxed for one-half hour and then cooled to room temperature. The reaction mixture is then diluted to 1000 ml. total volume with ice water. A solid precipitates which is separated, washed with water and dried. Crystallization from aqueous ethanol gives 6.38 gms. of 2-chloro-N-(2-pyridylmethyl)benzamide (65% of theory) in the form of pale orange crystals; m.p. 96.6° C.

Similarly, following the above procedure but replacing the 2-aminomethylpyridine as used therein with an equal molar proportion of 4-aminomethyl-2-chloropyridine (prepared by reducing the corresponding nitrile of formula (IVC) [See R. L. Augustine "Reduction - Technique and Application in Organic Synthesis", Marcel Dekker, Inc., New York (1968)] and replacing the 2-chlorobenzoyl chloride as used therein with 3-nitrobenzoyl chloride, 3-aminobenzoyl chloride 3-methylbenzoyl chloride, and 2,5-dimethoxybenzoyl chloride, respectively, there is obtained 3-nitro-N-[4-(2-chloropyridylmethyl)]benzamide, 3-amino-N-[4-(2-chloropyiridylmethyl)]benzamide, 3-methyl-N-[4-(2-chlorpyridylmethyl)]benzamide, and 2,5-dimethoxy-N-[4-(2-chloropyridylmethyl)]benzamide, respectively.

EXAMPLE 9

Part A

Following the procedure of Example 6, Part A, supra., but replacing the 3-chlorobenzoyl chloride as used therein with 6.68 gms. (0.03 mole) of 3-fluorosulfonylbenzoyl chloride and reducing the proportion of 2-aminomethylpyridine as used therein to 3.24 gms. (0.03 mole) there is obtained 3-fluorosulfonyl-N-(2-pyridylmethyl)benzamide in the form of a tan colored solid.

Part B

Following the procedure of Example 6, Part B, supra., but replacing the oil residue as used therein with the 3-fluorosulfonyl-N-(2-pyridylmethyl)benzamide prepared in Example 9, Part A, supra, there is obtained 5.15 gm. (52% of theory) of 3-fluorosulfonyl-N-(2-pyridylmethyl)benzamide hydrochloride in the form of colorless needles, m.p. 188.2° C.

EXAMPLE 10

Follwing the procedure of Example 1, supra., but replacing the 3-aminomethylpyridine as used therein with 3.24 gms. (0.03 mole) of 2-aminomethylpyridine and replacing the 3-chlorobenzoyl chloride as used therein with 5.76 gms. (0.03 mole) of 3-trifluoromethylbenzoyl fluoride there is obtained an amber colored oil which is 3-trifluoromethyl-N-(2-pyridylmethyl)benzamide. The oil is dissolved in 100 ml. of chloroform and the solution saturated with anhydrous hydrogen chloride. The resulting solution is then evaporated to dryness. The residue is crystallized from methanol to furnish 2.63 gm. (28% of theory) of 3-trifluoromethyl-N-(2-pyridylmethyl)benzamide hydrochloride in the form of colorless crystals; m.p. 166.4° C.

EXAMPLE 11

Following the procedure of Example 8, supra., but replacing the 2-chlorobenzoyl chloride as used therein with 6.26 gms. (0.03 mole) of 4-trifluoromethylbenzoyl chloride and reducing the proportion of 2-aminomethylpyridine to 3.24 gms. (0.03 mole) there is obtained 5.01 gms. (60 percent of theory) of 4-trifluoromethyl-N-(2-pyridylmethyl)benzamide in the form of colorless crystals; m.p. 108.2° C.

EXAMPLE 12

Following the procedure of Example 1, supra, but replacing the 3-aminomethylpyridine as used therein with an equal molar proportion of 2-aminoethylpyridine and replacing the 3-chlorobenzoyl chloride as used therein with an equal molar proportion of 4-chlorobenzoyl chloride there is obtained 4.56 gms. (44 percent of theory) of 4-chloro-N-(2-pyridyethyl)benzamide in the form of colorless crystals, m.p. 111.8° C.

EXAMPLE 13

Part A

Following the procedure of Example 6, Part A, supra., but replacing the 2-aminomethylpyridine as used therein with 4.32 gms. (0.04 mole) of 4-aminomethylpyridine and replacing the 3-chlorobenzoyl as used therein with 9.34 gms. (0.04 mole) of 4-trifluoromethylbenzoyl chloride there is obtained 4-trifluoromethyl-N-(4-pyridylmethyl)benzamide in the form of a pale yellow oil.

Part B

Following the procedure of Example 6, Part B, supra., but replacing the oil residue as employed therein with the 4-trifluoromethyl-N-(4-pyridylmethyl)benzamide obtained in Example 13, Part A, supra., there is obtained 4.97 gms. (39 percent of theory) of 4-trifluoromethyl-N-(4-pyridylmethyl)benzamide hydrochloride in the form of almost colorless, hygroscopic crystals, m.p. 163.5° C.

EXAMPLE 14

Following the procedure of Example 1, supra., but replacing the 2-aminomethylpyridine as used therein with an equal molar proportion of 4-aminomethylpyridine and replacing the 3-chlorobenzoyl chloride as used therein with an equal molar proportion of 2-chlorobenzoyl chloride there is obtained 3.84 gms. (39 percent of theory) of 2-chloro-N-(4-pyridylmethyl)benzamide in the form of yellow crystals; m.p. 113.3° C.

EXAMPLE 15

To a chilled mixture of 1.5 gm. (0.038 mole) of sodium hydroxide, 3.24 gm. (0.03 mole) of 4-aminomethylpyridine and 75 ml. of water there is added dropwise 5.76 gm. (0.03 mole) of m-trifluoromethylbenxoylfluoride, with stirring. Stirring is continued for 3 hours after completion of addition. The reaction mixture is then diluted to 500 ml. total volume with ice water. The precipitated solid is separated, washed with water and dried. Crystallization from Skellysolve B-ethyl acetate (2:1, v/v) gives 5.10 gm. (61% of theory) of 3-trifluoromethyl-N-(4-pyridylmethyl)benzamide as colorless crystals; m.p. 76.2° C.

EXAMPLE 16

To an ice-cold mixture of 1.5 gms. (0.038 mole) of sodium hydroxide, 3.24 gm. (0.03 mole) of 3-aminomethylpyridine and 100 ml. of water there is added dropwise 5.76 gm. (0.03 mole) of m-trifluoromethylbenzoyl fluoride with stirring. After 3 hours the mixture is diluted with ice water to 500 ml volume. An oil is separated from the resulting mixture which is 3-trifluoromethyl-N-(3-pyridylmethyl)benzamide. The oil is then dissolved in 75 ml. of ether. The resulting solution is then saturated with anhydrous hydrogen chloride. The mixture is then evaporated to remove solvent. The oily residue solidifies on standing. Crystallization from tetrahydrofuran gives 4.25 gm. (45 % of theory) of 3-trifluoromethyl-N-(3-pyridylmethyl)benzamide hydrochloride; m.p. 146.8° C.

EXAMPLE 17

To a chilled mixture of 2.2 g. (0.055 mole) of sodium hydroxide, 5.4 gm. (0.05 mole) of 4-aminomethylpyridine and 100 ml. of water there is added dropwise with stirring 10.43 gm. (0.05 mole) of p-trifluoromethylbenzoyl chloride. The mixture is stirred 3 hours and the solid which appears is separated, washed with water and dried. Crystallization from Skellysolve B-ethyl acetate (9:1 v/v) gives 5.70 gm. (41% of theory) of 4-trifluoromethyl-N-(4-N-(4-pyridylmethyl)benzamide as straw-colored crystals; m.p. 103.1° C.

EXAMPLE 18

To a mixture of 9.73 gms. (0.35 mole) of 3,5-ditrifluoromethylbenzoyl chloride, 100 ml. of tetrahydrofuran and 3.64 gns. (0.036 mole) of triethylamine there is added dropwise with stirring 3.81 gms. (0.035 mole) of 4-aminomethylpyridine. The resulting mixture is refluxed for 1 hour and then allowed to stand overnight at ambient temperature. At the end of this period, the reaction mixture is diluted to 1 liter volume with water. A solid precipitates which is spearated by filtration, washed with water and dried. Crystallization of the solid from a mixture of benzene Skellysolve B (1:4, v/v) gives 5.14 gms. of 3,5-ditrifluoromethyl-N-(4-pyridylmethyl)benzamide in the form of tan crystals; m.p. 230.0° C.

EXAMPLE 19

Following the procedure of Example 1, supra., but replacing the 2-aminomethylpyridine as used therein with 13.6 gms. (0.10 mole) of 2-methylaminoethylpyridine and replacing the 3-chlorobenzoyl chloride as used therein with 20.9 gms. (0.10 mole) of 4-trifluoromethylbenzoyl chloride there is obtained 16.39 gms. (33 percent of theory) of N-methyl-N-(2-pyridylethyl)-4-trifluoromethylbenzamide in the form of colorless crystals; m.p. 101.7° C.

Similarly, following the above procedure but replacing the 2-methylaminoethylpyridine as used therein with an equal molar proportion of 2-cyclohexylaminomethylpyridine, 2-phenylaminomethylpyridine, 2-benzylaminomethylpyridine, 2-(p-chlorophenyl)aminomethylpyridine, 2(p-methoxyphenyl)aminomethylpyridine, 2-(p-triflooromethylphenyl)aminomethylpyridine and 2-(p-trichloromethylphenyl)aminomethylpyridine, respectively, all of which may be prepared by reduction of the corresponding amides of formula (IVB), supra. [See H. C. Brown, "Hydroboration", W. A. Benjamin, Inc., New York (1962)], there is obtained N-cyclohexyl-; N-phenyl-; N-benzyl-; N-p-chlorophenyl; N-p-methoxyphenyl-; N-p-trifluoromethylphenyl-; and N-p-trichloromethylphenyl-N(2-pyridylmethyl)-4-trifluoromethylbenzamide, respectively.

EXAMPLE 20

Following the procedure of Example 1, supra., but replacing the 2-aminomethylpyridine as used therein with 12.2 gms. (0.1 mole) of 2-aminoethylpyridine and replacing the 3-chlorobenzoyl chloride as used therein with 20.85 gms. (0.1 mole) of 4-trifluoromethylbenzoyl chloride there is obtained 25.64 gms. (87 percent of theory) of N-(2-pyridylmethyl)-4-trifluoromethylbenzamide in the form of off-white colored crystals and needles; m.p. 120.3° C.

EXAMPLE 21

Following the procedure of Example 1, supra.,. but replacing the 3-chlorobenzoyl chloride as used therein with 7.34 gms. (0.03 mole) of 4-phenylazobenzoyl chloride and decreasing the proportion of 3-aminomethylpyridin as used therein to 3.24 gms. (0.03 mole) there is obtained 4.39 gms. (46 percent of theory) of 4-phenylazo-N-(3-pyridylmethyl)benzamide in the form of orange crystals, m.p. 182.3° C.

EXAMPLE 22

To 14.7 gms. (0.05 mole) of N-(2-pyridylethyl)-4-trifluoromethylbenzamide (Example 20, supra.) in 100 ml. of acetic acid there is added 7.8 ml. of 30 percent hydrogen peroxide. After standing overnight at ambient temperature, the solution is heated at 80° C. for 8 hours. Acetic acid is then removed under vacuum and the residue suspended in aqueous sodium bicarbonate. The solids are then separated by filtration, washed with water and dried. The dried material is then crystallized from mixture of benzene Skellysolve B (9:5, v/v) to give 14.17 gms. (91 percent of theory) of N-(2-pyridylethyl)-4-trifluoromethylbenzamide-N-oxide in the form of light yellow prisms; m.p. 120.4° C.

Similarly, repeating the above procedure but replacing the N-(2-pyridylethyl)-4-trifluoromethylbenzamide as used therein with any other compound of the formula (1) and pharmaceutically acceptable acid addition salts thereof as prepared in Examples 1–21, supra., the corresponding N-oxide is obtained.

The following examples illustrate the compositions and uses of the compounds of the invention and the method of the invention.

EXAMPLE 23—TABLETS

One thousand tablets for oral use, each containing 250 mg. of 2-chloro-N-(4-pyridylmethyl)benzamide as the essential active ingredient are prepared from the following ingredients:

| | |
|---|---|
| 2-chloro-N-(4-pyridylmethyl)-benzamide | 250 gms. |
| Lactose | 200 gms. |
| Microcrystalline Cellulose N.F. | 50 gms. |
| Starch | 5 gms. |
| Magnesium Stearate powder | 1 gm. |

The ingredients are thoroughly mixed and slugged. The slugs are broken down by forcing through a screen and the resulting granules are then compressed into tablets.

These tablets are useful in controlling atonic uterine hemorrhage in adult humans when given at a dose of 1 to 3 tablets. High blood levels of $PGF_{2\alpha}$ are observed for from 6 to 8 hours after administration.

The tablets are also useful for treating male mammals for infertility when 1 to 3 tablets are given 3 to 4 times a week.

EXAMPLE 24—CAPSULES

One thousand two-piece hard gelatin capsules for oral use, each capsule containing 250 mg. of 2-chloro- N-(4-pyridylmethyl)benzamide are prepared from the following ingredients:

| 2-chloro-N-(4-pyridylmethyl)-benzamide | 250 gms. |
|---|---|
| Lactose | 200 gms. |
| Talc | 25 gms. |
| Magnesium stearate | 2 gms. |

The finely powdered materials are mixed thoroughly, then filled into hard gelatin capsules of appropriate size. The capsules are given to adult humans suffering from burns at a dose of 1 to 3 capsules given 3 to 14 times a week, resulting in an acceleration of healing and epidermal proliferation.

EXAMPLE 25—AQUEOUS SOLUTION

An aqueous oral preparation containing in each teaspoonful (5ml.) 500 mg. of essential active ingredient is prepared from the following:

| 2-chloro-N-(4-pyridylmethyl)-benzamide | 500 gms. |
|---|---|
| Glycerin | 2000 ml. |
| Tragacanth powder | 50 gms. |
| Propylparaben | 3 gms. |
| Sucrose | 6.5 gms. |
| Orange oil flavor | 5 gms. |
| Deionized water q.s. | 5000 ml. |

The above oral preparation may be given to adult humans at a dose of 1 to 3 teaspoons 3 to 14 times weekly to accelerate the healing of epidermal wounds.

EXAMPLE 26—INJECTABLE

A sterile suspension suitable for intramuscular injection and containing in each milliliter 250 mg. of 2-chloro-N-(4-pyridylmethyl)benzamide is prepared from the following ingredients:

| 2-chloro-N-(4-pyridylmethyl)-benzamide | 250 gms. |
|---|---|
| Benzyl benzoate | 200 ml. |
| Methylparaben | 1.5 gms. |
| Propylparaben | 0.5 gms. |
| Cottonseed oil q.s. | 1000 ml. |

The above sterile injectable is useful in controlling the development of thrombi following saphenectomy when given at a dose of 1 to 4 ml. administered 2 to 6 hours prior to said saphenectomy.

EXAMPLE 27—SUPPOSITORY

One thousand suppositories, each weighing 4.0 gms. and containing 500 mg. of 2-chloro-N-(4-pyridylmethyl)benzamide as the essential active ingredient are prepared from the following ingredients:

| 2-chloro-N-(4-pyridylmethyl)-benzamide | 500 gms. |
|---|---|
| Propylene glycol | 2000 gms. |
| Polyethylene glycol 4000 | 1000 gms. |
| Polyethylene glycol 400 | 500 gms. |

The 2-chloro-N-(4-pyridylmethyl)benzamide is added to the propylene glycol and the mixture milled until uniformly dispersed. The polyethylene glycol 4000 is melted and the propylene glycol dispersion added. The suspension is poured into molds and allowed to cool and solidify.

These suppositories are useful for controlling development of thrombi in mammals when given rectally at a dose of 1 suppository 3 to 7 times a week.

EXAMPLE 28

Various compounds of the formula (I) are admixed with water and administered orally to groups of 5 male Carworth rats (weighing 250–275 gms. each) at a dosage of 50 mg. per kilogram of body weight. The rats are prepared by fasting overnight (16 hours) prior to administration. About 3 hours after administration, tails are clipped and the rats bled. 5 ml. of blood is collected in citrated syringes (0.1 ml. of 3.8 percent w/v sodium citrate per ml. of whole blood). The collected blood is centrifuged at 900 RPM for 15 minutes and the platelet rich plasma separated and pooled for each group of 5 rats. For each 1.0 mls. of pooled plasma there is added 0.5 ml. of 0.15M sodium phosphate buffer (pH 7.4). The resulting mixture is allowed to stand at room temperature for 30 minutes and then 0.5 mls. of sodium fluoride (4 mgs./ml. aqueous solution) is added. The mixture is then incubated at 37° C. for 60 minutes, cooled under running tap water and centrifuged at 2500 RPM for 20 minutes. The supernatant solution is separated and analysed for $PGF_{2\alpha}$ concentration by the method of Kirton et al., Biochemical and Biophysical Res. Comm., Vol. 47, 903 (1972).

The compounds employed and the results obtained are given in Table I below. Group A does not represent the invention but is a control group of 5 rats which did not receive an administration of a compound (I).

TABLE 1

| Group | Compound (I) Administered | Concentration of $PGF_{2\alpha}$ Found (ng./ml.) |
|---|---|---|
| A (control) | none | 32.3 ± 3.3 |
| B | 2-chloro-N-(3-pyridylmethyl)-benzamide | 58.8 ± 5.3 |
| C | 3-methyl-N-(4-pyridylmethyl)-benzamide | 61.5 ± 6.5 |
| D | 2-chloro-N-(4-pyridylmethyl)-benzamide | 80.2 ± 6.9 |

Similarly, repeating the above procedure but replacing the compounds of formula (I) as used therein with any other compounds of the formula (I), or of the formula (VI) and the pharmaceutically acceptable acid addition salts thereof prepared according to Examples 1–22, supra., similar observations of increased prostaglandin production are made.

A further group of compounds of the invention are those compounds of Formula I wherein $R_1$, $R_4$ and $R_5$ are hydrogen; $R_2$ and $R_3$ are the same or different and are hydrogen or alkyl of one to four carbon atoms, inclusive; $R_6$ is selected from the group consisting of hydrogen, alkyl of one to four carbon atoms, inclusive, alkoxy of one to four carbon atoms, inclusive, halogen, nitro and trifluoromethyl; $n$ is one or 2.

A still further group of compounds are those of the above group wherein the pyridine moiety is attached to the alkylene group at the 4-position.

The N-oxides of these compounds are also a portion of the invention. These groupings of compounds are used in the same manner as the larger generic groupings and formulated into like pharmaceutical compositions.

We claim:
1. A compound of the formula

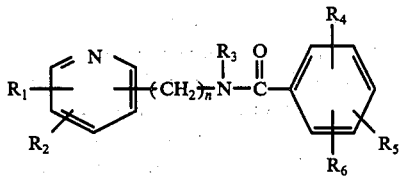

or a pharmaceutically acceptable acid addition salt thereof, wherein R₁ and R₂ are each hydrogen, halogen, hydrocarbyl of one to six carbon atoms, inclusive alkoxy of 1 to 12 carbon atoms, inclusive, nitro, amino, alkylamino of 1 to 12 carbon atoms, inclusive, dialkylamino, each alkyl of 1 to 12 carbon atoms, inclusive, acylamino with alkyl of 1 to 12 carbon atoms, inclusive, or trihalomethyl; R₃ is hydrogen, alkyl of 1 to 4 carbon atoms, inclusive, cycloalkyl of 3 to 8 carbon atoms, inclusive, aryl of 6 to 12 carbon atoms, inclusive, aralkyl of 7 to 12 carbon atoms, inclusive, or aryl of 6 to 12 carbon atoms, inclusive, substituted with halogen, alkoxy of 1 to 4 carbon atoms, inclusive, halogen-substituted alkyl of 1 to 4 carbon atoms, inclusive, or halogen-substituted alkoxy of 1 to 4 carbon atoms, inclusive, R₄ is hydrogen, bromine, fluorine, iodine, hydrocarbyl of 1 to 12 carbon atoms, inclusive, or halogen-substituted hydrocarbyl of 1 to 12 carbon atoms, inclusive; R₅ is nitro, amino, acylamino with alkyl of 1 to 12 carbon atoms, inclusive, alkylamino with alkyl of 1 to 12 carbon atoms, inclusive, dialkylamino with each alkyl of 1 to 12 carbon atoms, inclusive, aryloxy of 6 to 12 carbon atoms, inclusive, or a group R₄ as previously defined; R₆ is chlorine, or a group R₅ as defined above; n is an integer of from 1 to 2; provided that when R₄, R₅ and R₆ are each hydrogen or when R₄ and R₅ are hydrogen and R₆ is alkyl of one to twelve carbon atoms, inclusive, amino or nitro, then at least one of R₁ and R₂ is halogen, phenyl, alkoxy of 1 to 12 carbon atoms, inclusive, alkylamino with alkyl of 1 to 12 carbon atoms, inclusive, dialkylamino with each alkyl of 1 to 12 carbon atoms, inclusive, acylamino with alkyl of one to 12 carbon atoms, inclusive, or trihalomethyl.

2. A compound of claim 1 wherein R₁, R₂ and R₄ are hydrogen; R₃ is hydrogen, alkyl of one to four carbon atoms, inclusive, cycloalkyl of 3 to 8 carbon atoms, inclusive, aryl of 6 to 12 carbon atoms, inclusive, and aralkyl of seven to 12 carbon atoms, inclusive; R₅ is halogen or mono to tri halogen-substituted hydrocarbyl of 1 to 12 carbon atoms, inclusive; and R₆ is hydrogen, halogen, cycloalkyl of three to eight carbon atoms, inclusive, alkenyl of 2 to 12 carbon atoms, inclusive, aryl or 6 to 12 carbon atoms, inclusive, aralkyl of seven to twelve carbon atoms, inclusive, mono to tri halogen-substituted hydrocarbyl of 1 to 12 carbon atoms, inclusive, acylamino with alkyl of 1 to 12 carbon atoms, inclusive, alkylamino with alkyl of 1 to 12 carbon atoms, inclusive, dialkylamino with each alkyl of 1 to 12 carbon atoms, inclusive, or aryloxy of 6 to 12 carbon atoms, inclusive; n is 1 and the methylene is attached to the pyridine at the 4 position.

3. A compound in accordance with claim 1 wherein R₁, R₂ and R₄ are hydrogen; R₃ is hydrogen, alkyl of one to four carbon atoms, inclusive, cycloalkyl of three to eight carbon atoms, inclusive, aryl of six to 12 carbon atoms, inclusive, and aralkyl of seven to 12 carbon atoms, inclusive; R₅ is fixed ortho to the benzamide linkage and is halogen or halogen-substituted hydrocarbyl of one to 12 carbon atoms, inclusive; and R₆ is hydrogen, halogen, cycloalkyl of three to eight carbon atoms, inclusive, alkenyl of two to 12 carbon atoms, inclusive, aryl of six to 12 carbon atoms, inclusive, aralkyl of seven to 12 carbon atoms, inclusive, halogen-substituted hydrocarbyl of one to 112 carbon atoms, inclusive, acylamino with alkyl of one to 12 carbon atoms, inclusive, alkylamino with alkyl of one to 12 carbon atoms, inclusive, dialkylamino with each alkyl of one to 12 carbon atoms, inclusive; n is 1 and the methylene is attached to the pyridine at the 4 position.

4. A compound in accordance with claim 3 wherein R₁, R₂ and R₄ are hydrogen; R₃ is hydrogen or alkyl of one to for carbon atoms, inclusive; R₅ is fixed ortho to the benzamide linkage and is halogen or halogen-substituted hydrocarbyl of one of six carbon atoms, inclusive; R₆ is hydrogen, halogen or halogen-substituted hydrocarbyl of one to six carbon atoms, inclusive; n is 1 and the methylene is attached to the pyridine at the 4 position.

5. The compound of claim 1 which is 3-chloro-N-(3-pyridylmethyl)benzamide.

6. The compound of claim 1 which is 4-chloro-N-(3-pyridylmethyl)benzamide.

7. The compound of claim 1 which is 2-chloro-N-(3-pyridylmethyl)benzamide.

8. The compound of claim 1 which is N-(3-pyridylmethyl)-4-trifluoromethylbenzamide.

9. The compound of claim 1 which is 3-fluoro-N-(3-pyridylmethyl)benzamide.

10. The compound of claim 1 which is 3-chloro-N-(2-pyridylmethyl)benzamide.

11. The compound of claim 1 which is 3-chloro-N-(2-pyridylmethyl)benzamide hydrochloride.

12. The compound of claim 1 which is 4-chloro-N-(2-pyridylmethyl)benzamide.

13. The compound of claim 1 which is 2-chloro-N-(2-pyridylmethyl)benzamide.

14. The compound of claim 1 which is 3-trifluoromethyl-N-(2-pyridylmethyl)benzamide.

15. The compound of claim 1 which is 3-trifluoromethyl-N-(2-pyridylmethyl)benzamide hydrochloride.

16. The compound of claim 1 which is 4-trifluoromethyl-N-(2-pyridylmethyl)benzamide.

17. The compound of claim 1 which is 4-chloro-N-(2-pyridyethyl)benzamide.

18. The compound of claim 1 which is 4-trifluoromethyl-N-(4-pyridylmethyl)benzamide.

19. The compound of claim 1 which is 4-trifluoromethyl-N-(4-pyridylmethyl)benzamide hydrochloride.

20. The compound of claim 1 which is 2-chloro-N-(4-pyridylmethyl)benzamide.

21. The compound of claim 1 which is 3-trifluoromethyl-N-(4-pyridylmethyl)benzamide.

22. The compound of claim 1 which is 3-trifluoromethyl-N-(3-pyridylmethyl)benzamide.

23. The compound of claim 1 which is 3-trifluoromethyl-N-(3-pyridylmethyl)benzamide hydrochloride.

24. The compound of claim 1 which is 4-trifluoromethyl-N-(4-pyridylmethyl)benzamide.

25. The compound of claim 1 which is 3,5-ditrifluoromethyl-N-(4-pyridylmethyl)benzamide.

26. The compound of claim 1 which is N-methyl-N-(2-pyridylethyl)-4-trifluoromethylbenzamide.

27. The compound of claim 1 which is N-(2-pyridylethyl)-4-trifluoromethylbenzamide.

28. A compound of the formula

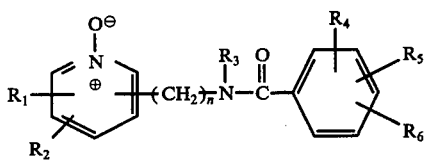

or a pharmaceutically acceptable acid addition salt thereof wherein $R_1$ and $R_2$ are hydrogen, halogen, hydrocarbyl of one to six carbon atoms, inclusive, alkoxy of one to 12 carbon atoms, inclusive, nitro, amino, alkylamino with alkyl of one to 12 carbon atoms, inclusive, dialkylamino with each alkyl of one to 12 carbon atoms, inclusive, acylamino with alkyl of one to 12 carbon atoms, inclusive, and trihalomethyl; $R_3$ is hydrogen, alkyl of one to four carbon atoms, inclusive, cycloalkyl of three to eight carbon atoms, inclusive, aryl of six to 12 carbon atoms, inclusive, aralkyl of seven to 12 carbon atoms, inclusive, or aryl of six to 12 carbon atoms, inclusive, substituted with a member selected from the group consisting of halogen, alkoxy of one to four carbon atoms, inclusive, halogen substituted alkyl of one to four carbon atoms, inclusive or halogen-substituted alkoxy of one to four carbon atoms, inclusive; $R_4$ is hydrogen, bromine, fluorine, iodine, hydrocarbyl of one to 12 carbon atoms, inclusive, alkoxy of one to 12 carbon atoms, inclusive, or halogen-substituted hydrocarbyl of one to 12 carbon atoms, inclusive; $R_5$ is nitro, amino, acylamino with alkyl of one to 12 carbon atoms, inclusive, alkylamino with alkyl of one to 12 carbon atoms, inclusive, dialkylamino with each alkyl of one to 12 carbon atoms, inclusive, aryloxy or a group $R_4$ as previously defined; $R_6$ is chlorine or a group $R_5$ as defined above; and $n$ is an integer of from 1 to 2, inclusive.

29. A compound of claim 28 which is N-(2-pyridylethyl)-4-trifluoromethylbenzamide-N-oxide.

* * * * *